US007155966B1

(12) United States Patent
Etyemezian et al.

(10) Patent No.: US 7,155,966 B1
(45) Date of Patent: Jan. 2, 2007

(54) WIND SHEAR INDUCING SOIL STABILITY MEASURING DEVICE

(75) Inventors: Vicken Etyemezian, Las Vegas, NV (US); Hampden Dwight Kuhns, Reno, NV (US); Marc Lynn Pitchford, Las Vegas, NV (US); Sean Jason Ahonen, Roswell, GA (US); George Nikolich, Las Vegas, NV (US)

(73) Assignee: The Board of Regents of the University and Community College System of Nevada on behalf of the Desert Research Institute, Reno, NV (US)

( * ) Notice: Subject to any disclaimer, the term of this patent is extended or adjusted under 35 U.S.C. 154(b) by 36 days.

(21) Appl. No.: 10/865,117

(22) Filed: Jun. 10, 2004

Related U.S. Application Data

(60) Provisional application No. 60/477,691, filed on Jun. 10, 2003.

(51) Int. Cl.
*G01M 9/02* (2006.01)
(52) U.S. Cl. ....................................................... 73/147
(58) Field of Classification Search ................. 73/147, 73/432.1
See application file for complete search history.

(56) References Cited

U.S. PATENT DOCUMENTS 4,435,080 A * 3/1984 Maly et al. .................. 356/426
5,894,096 A * 4/1999 Kotraba et al. ........... 73/864.63

OTHER PUBLICATIONS

Loosmore, Gwen A. and Hunt, James R., Dust Resuspension Without Saltation, J. of Geophysical Research, V. 105, No. D16, pp. 20,633-20,671, Aug. 27, 2000.
Pietersma, D., Stetler, L.D., Saxton, K.E., Design and Aerodynamics of a Portable Wind Tunnel for Soil Erosion and Fugitive Dust Research, Transaction of the American Society of Agricultural Engineers, v. 39(6):2075-2083, 1996.

* cited by examiner

*Primary Examiner*—Hezron Williams
*Assistant Examiner*—Paul M. West
(74) *Attorney, Agent, or Firm*—Rob L. Phillips; Greenberg Traurig

(57) ABSTRACT

An apparatus for measuring soil stability of a test surface comprising a housing defining an interior chamber, the housing having an open bottom wherein the housing is configured to be placed over the test surface proximate the open bottom. A means for generating wind shear disposed in the interior chamber, the wind shear generating means configured to generate wind shear proximate the test surface and at least one particle monitor in communication with the interior chamber.

16 Claims, 5 Drawing Sheets

WIND SHEAR INDUCING SOIL STABILITY MEASURING DEVICE

CROSS-REFERENCE TO RELATED APPLICATIONS

This application claims the benefit of U.S. Provisional Application No. 60/477,691 filed Jun. 10, 2003.

FIELD OF INVENTION

The present invention relates generally to devices for generating wind shear over a dirt-covered surface and for measuring the particle matter emission potential of that surface.

BACKGROUND

The potential for a dirt-covered surface to emit particles when wind passes over the surface has been difficult to measure in the past. In this case, a dirt-covered surface refers to any surface where a layer of soil, dust, or other particles lie atop the surface. This can include but is not limited to the open desert, a paved road with some dust particles on the surface, or a construction site. Small particles that are emitted from these surfaces when a wind or breeze blows them off can be inhaled by humans or can redeposit at locations that are undesirable. Small particles can be significant contributors to air pollution, allergens, and the spreading of disease. Air pollution regulations for particulate matter are violated in numerous locations. In many of these locations the wind suspended dust is thought to be responsible for a substantial share of the problem. Therefore, it is of interest to be able to measure how much of the small particle material is suspended under given wind conditions. The magnitude of wind suspended dust emissions from a surface depends on the wind shear and the wind suspended dust emission potential of the surface.

Three methods have been historically available to estimate the wind-suspended dust emission potential of surfaces. The first is the assessment of ambient particulate matter data under various wind conditions. The second is assessment of the near-ground mobilization of sand through the use of an array of microphones that register the impact of sand grains during windblown dust events. The third is the assessment of particulate matter concentrations generated in open-bottomed wind tunnels. The first and second methods rely on dust suspended from naturally occurring winds. Measurements are performed at times that are coincident with such events. Use of naturally occurring winds to suspend dust is problematic because the wind shears that are encountered in nature are not generally well known or controllable. Furthermore dust may be suspended from many surfaces upwind of the area instrumented for measurements thereby confounding the interpretation of the measurements. The third method utilizes open-bottom wind tunnels to generate wind shear to suspend dust that is subsequently measured by particulate matter monitors. Existing wind tunnels operate by using a fan located at one end of the tunnel, to either pull or push air along the length of an enclosure that is rectangular in cross-section. One side of the rectangular cross-section is open and faces the test surface. Wind that is forced over the test surface by the fan indirectly generates a shear stress above the soil surface. Since several meters of tunnel may be required in order for the airflow inside the tunnel to behave as desired, these devices are frequently encumbered by their size. Because wind tunnels of this type are large, ranging from 2 to 10 meters in length and have cross sections from 0.2 to 2 meters on a side, these tunnels are difficult to deploy and require from several man-hours to several man-days to set-up for field operation. As a result, relatively few measurements of dust or particulate matter emission potential are made.

There is a need for a device that is easily portable, and that provides a rapid and inexpensive approach for measuring windblown dust emissions potentials at multiple locations in a short period of time.

SUMMARY

The embodiments in accordance with the present invention provide a portable apparatus for generating wind shear over a small dirt-covered surface area and then measuring the quantity of dust that can be suspended. An embodiment in accordance with the present invention includes a circular housing having a top and a sidewall defining an interior an exterior and an open bottom for placement near, the dirt-covered surface to be tested. In a first embodiment, a ring or disc having a generally flat wind shear generating surface is contained within the housing, and positioned so that the ring surface is above the test surface with the plane of the ring being generally parallel to the test surface. A drive unit rotates the ring above the plane of the surface to be tested, the rotation of the ring sends air in a primarily parallel direction towards the test surface and thereby inducing wind shear stress above the dirt covered surface. Increasing the ring's rate of rotation increases the wind shear across the test surface. Particles on the dirt-covered surface that are stimulated by the wind shear are suspended into the air above the test surface and are sampled by a particle monitor in communication with the housing. The particle monitor measures size, distribution, concentration and the optical properties of the dust grains emitted from the test surface. A skirt attached to the housing is sealed to the test surface to ensure that dust generated by the wind shear is contained within the interior chamber and preclude dust exterior to the housing from being introduced into the interior chamber. The degree of ventilation within the chamber is controlled by a blower that allows dust free air to be introduced into the chamber and by an exhaust manifold that allows removal of particles in the chamber. Embodiments of the present invention include a location measurement device that records the locations of each test surface where a measurement is performed. All operations of the device are controlled by an operator.

BRIEF DESCRIPTION OF THE DRAWINGS

The present invention is described with respect to particular exemplary embodiments thereof and reference is accordingly made to the drawings (which are not necessarily drawn to scale) in which.

DETAILED DESCRIPTION

Figure 1:
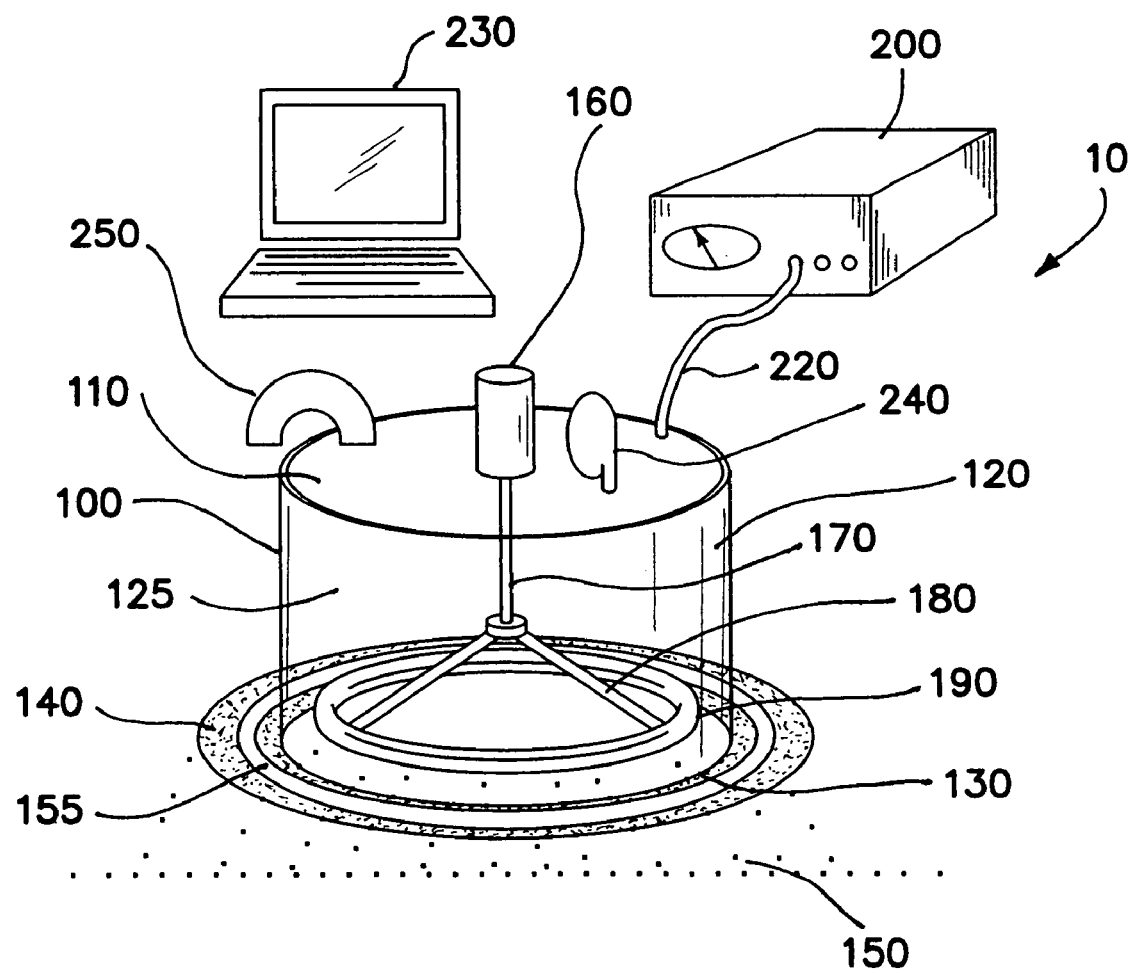
FIG. 1 shows a top perspective view of an embodiment the present invention.

Referring now to the drawings, FIG. 1 illustrates an embodiment of the present invention in which device 10 having a housing 100 comprising a top 110, a sidewall 120 defining an interior chamber 125, a bottom that is open to a test surface 130 and a skirt 140 for sealing the interior chamber 125 to a test surface 150. The device 10 also comprises a motor 160 coupled with a shaft 170 connected with a support system 180 supporting a ring 190 that is contained within the housing 100. Particulate monitor 200 is connected with housing 100 by a sample tube 220. Data recording system 230 is in communication with housing 100 by any conventional means. In some embodiments, blower 240 and exhaust manifold 250 are connected with housing 100. In practice, the skirt 140 of housing 100 is placed onto test surface 150 with ring 190 being positioned above, and in a generally parallel plane, with the test surface 150. Skirt 140 is affixed to the housing 100 by any conventional means and is placed onto test surface 150. A seal is created between skirt 140 and test surface 150. In one embodiment, the seal is created using silicone on the portion of skirt 140 that is in contact with test surface 150. In other embodiments, the seal is created by placing a heavy object on the portion of the skirt 140 that is not in contact with test surface 150.

Returning now to FIG. 1, housing 100 of device 10 is placed onto test surface 150 with the open bottom 130 of housing 100 being positioned above and proximate test surface 150 such that ring 190 is above test surface 150. As the motor 160 rotates shaft 170, ring surface 195 rotates within the housing 100, generating airflow that is generally parallel to test surface 150 thereby creating wind shear 310, best illustrated by FIG. 6. The airflow results in dust particles 320 on test surface 150 moving above the test surface 150, with some particles 325 becoming briefly suspended in air above test surface 150. Dust particles 325 generated from the wind shear created within the chamber 125 are then drawn into sample tube 220 of particle monitor 200, best seen in FIG. 1. Within the sample tube 220 of particle monitor 200, dust particles 325 are measured for size, distribution, concentration and their optical properties. In some embodiments, housing 100 is generally cylindrical and constructed of any suitably rigid material such as rubber, plastic or metal. In other embodiments, housing 100 is generally rectangular while in other embodiments, housing 100 can be constructed of any suitable shape and construction. A height of interior chamber 125 when measured from test surface 150 is preferably from about 0.1 meters to about 0.4 meters.

Figure 2A:
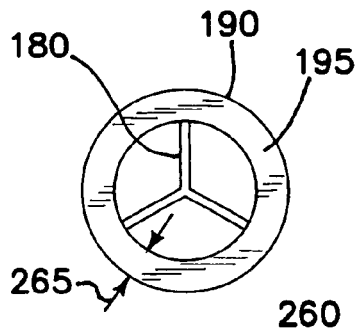
FIG. 2(a) shows a bottom perspective view of an embodiment a ring of present invention.
Figure 2B:
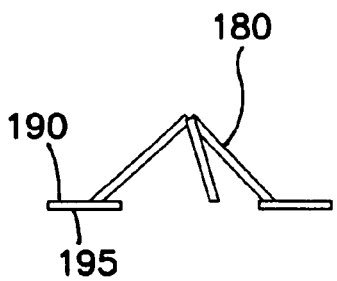
FIG. 2(b) shows a side schematic view of an embodiment a ring of present invention.
Figure 2C:
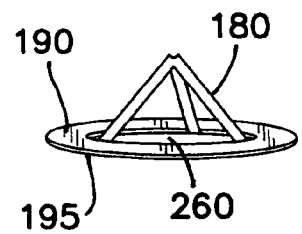
FIG. 2(c) shows a side perspective view of an embodiment a ring of present invention.
Figure 3A:
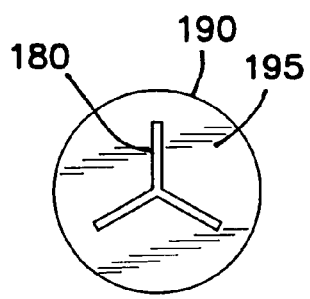
FIG. 3(a) shows a bottom perspective view of an embodiment a ring of present invention.
Figure 3B:
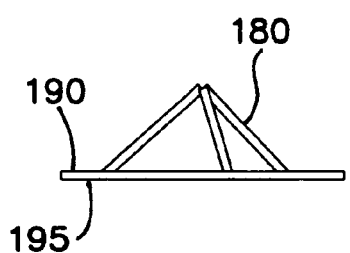
FIG. 3(b) shows a side schematic view of an embodiment a ring of present invention.
Figure 3C:
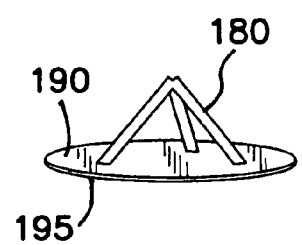
FIG. 3(c) shows a side perspective view of an embodiment a ring of present invention.
Figure 4A:
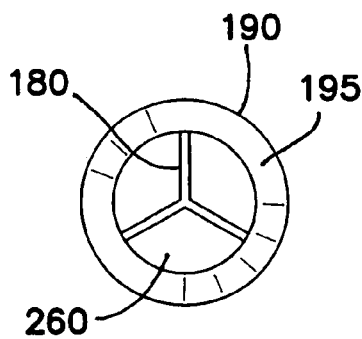
FIG. 4(a) shows a bottom perspective view of an embodiment a ring of present invention.
Figure 4B:
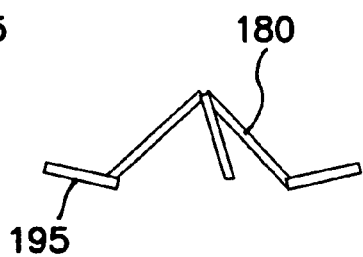
FIG. 4(b) shows a bottom perspective view of an embodiment a ring of present invention.
Figure 4C:
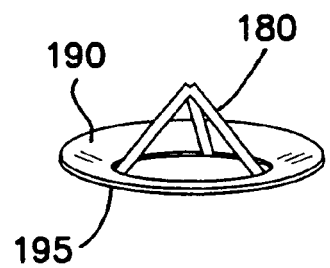
FIG. 4(c) shows a bottom perspective view of an embodiment a ring of present invention.

FIGS. 2(a)–(c) illustrate an embodiment of ring 190 having surface 195, support system 180 aperture 260 and a width 265. FIGS. 3(a)–(c), illustrate another embodiment of ring 190 having surface 195, support system 180 and width 265. FIGS. 4(a)–(c) illustrate an embodiment of ring 190 having aperture 260, support system, i.e., spokes 180, and surface 195, that is beveled with respect to the test surface, not shown. Ring surface 195 of each of the different rings create a frictional shear force or wind shear, for the purpose of suspending dust particles above the test surface, not shown. In practice, surfaces 195 of a ring 190 are positioned above and generally parallel with respect to test surface 150, best shown in FIG. 1. A diameter of ring 190 is from about 0.2 meters to about 0.6 meters. Preferably, the diameter of ring 190 is slightly smaller than the interior chamber 125 of the housing 100. Width 265 is from about 8 centimeters to about 10 centimeters. Those skilled in the art however will recognize that width 265 surface 190 and diameter are variable.

Figure 5:
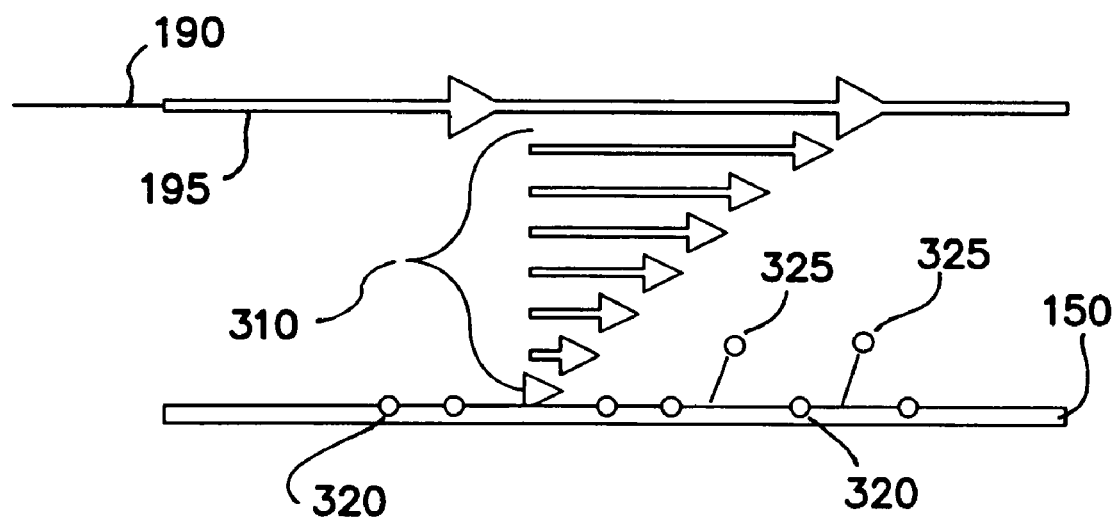
FIG. 5 shows a diagram of wind shear generated by an embodiment of the present invention.
Figure 6:
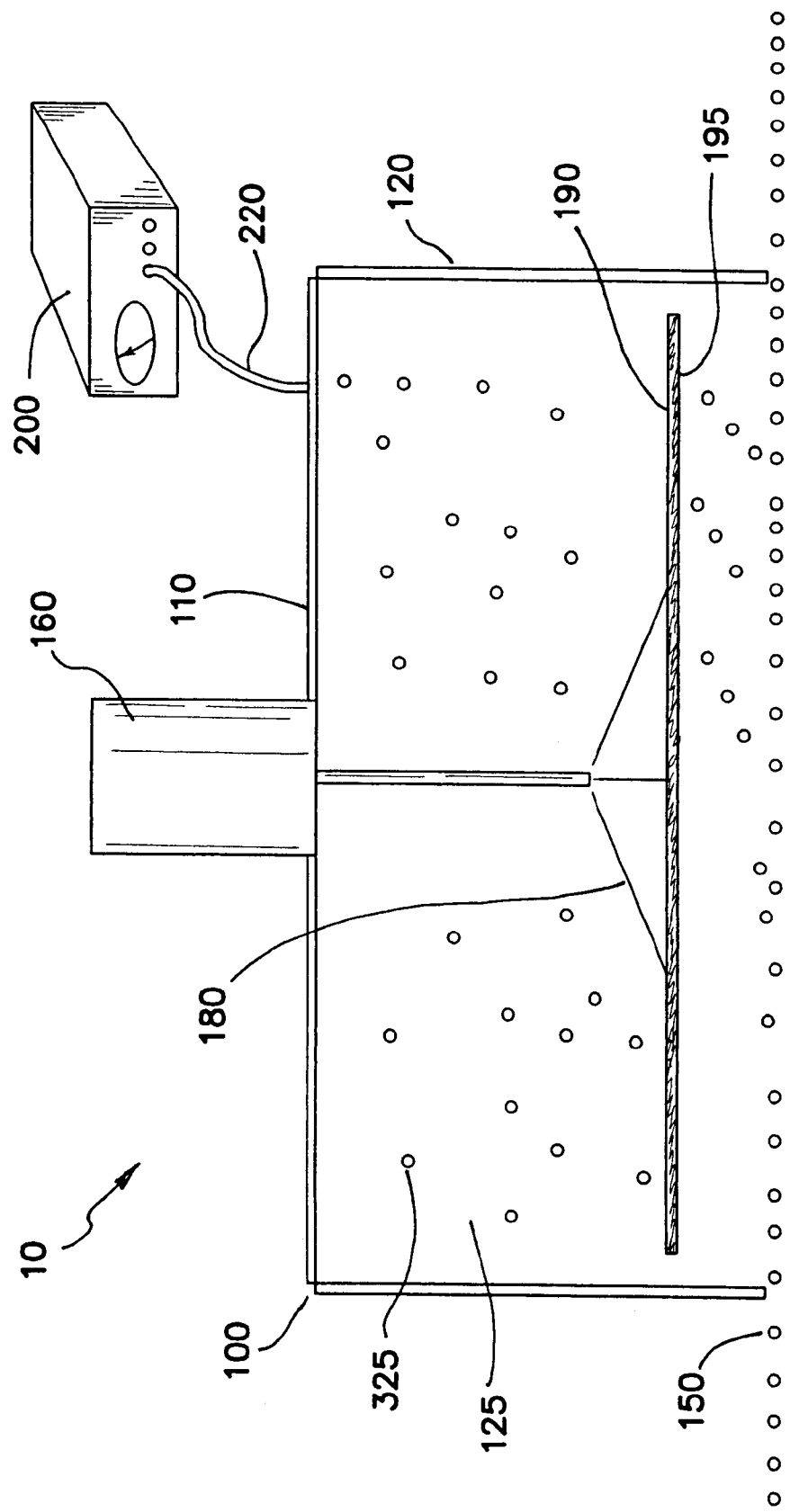
FIG. 6 shows a side view of an embodiment the present invention.

The operating principle of the device 10 is illustrated in FIGS. 5 & 6. As surface 195 of ring 190 moves over the test surface 150 containing dust particles 320, a wind speed gradient 310 forms between the moving surface 195 of ring 190 and the test surface 150. Airflow generated by movement of surface 195, results in wind shear stresses at the test surface 150. At sufficient magnitude, these shear stresses cause movement of small particles 320 at the test surface 150 of interest. In some cases, the magnitudes of the velocity gradient or wind shear 310, and the corresponding stresses at the test surface 150 increase with the rate of rotation of ring 190. Referring now to FIG. 6, as ring 190 rotates within the interior chamber 125 of the housing 100, wind shear generated by surface 195 of ring 190 increases the wind shear above test surface 150. This increase in wind shear 310 causes additional dust particles 320 on test surface 150 to be released from the test surface 150 where they may then move up into the interior chamber 125 and enter sample tube 220 to be sampled by particle monitor 290.

Figure 7:
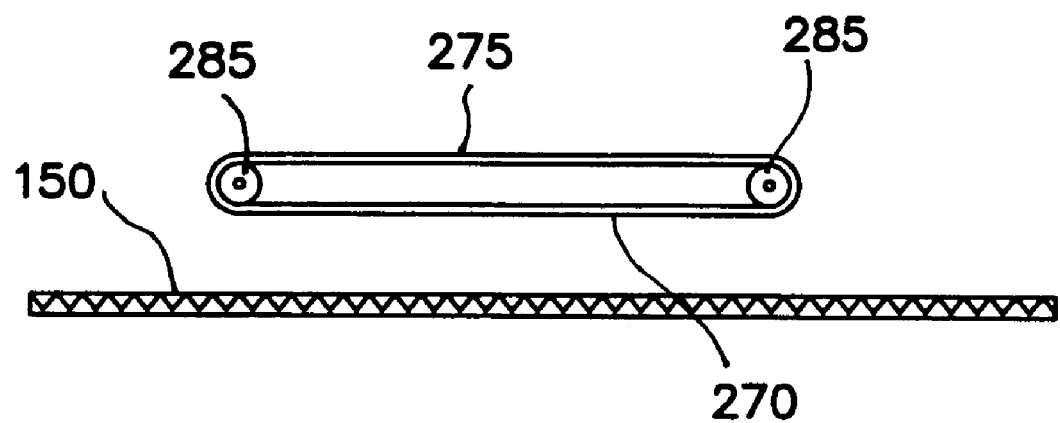
FIG. 7 shows a schematic side view of an embodiment of the present invention.
Figure 8:
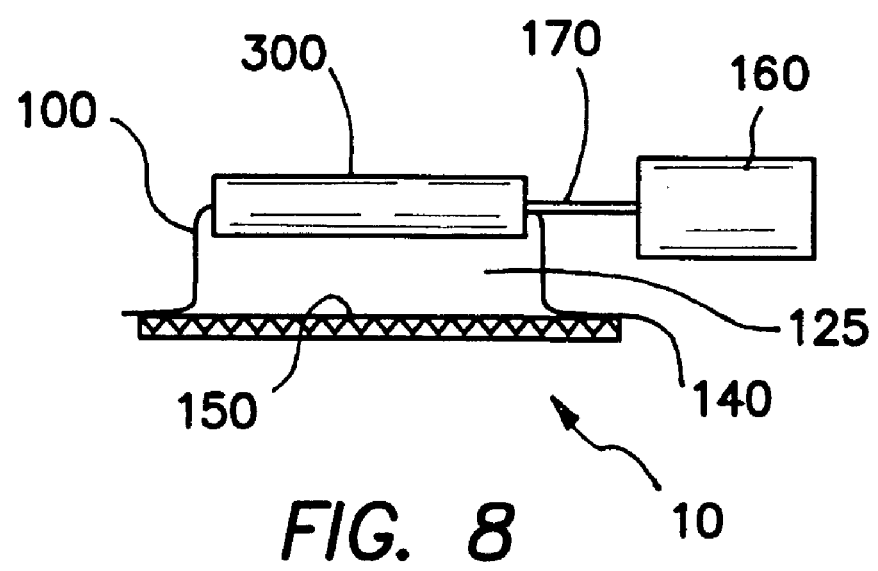
FIG. 8 shows a schematic side view of an embodiment of the present invention.

FIGS. 7 & 8 illustrate another embodiment of device 10 having housing 100 comprising a top 110, a sidewall 120 defining an interior chamber 125, and open bottom 130. Skirt 140 is sealed to test surface 150 to prevent the passage of dust particles 320 exterior to housing 100 from passing into or out of chamber 125. Motor 160 drives shaft 170 to rotate belt 270 over rollers 280 & 285. In this embodiment, wind shear is generated in the manner described above, as surface 270 of belt 275 moves above and across test surface 150. As in other embodiments, skirt 140 of housing 100 forms a tight joint with test surface 150 to prevent dust particles exterior to housing 100 from entering chamber 125. In one embodiment, belt 270 and rollers 280 & 285 are contained within a belt and roller assembly 300.

In some embodiments, ring 190 is generally rigid and constructed from any suitably rigid material that will rotate at high rpm without wobbling. Suitable materials include plastic, metal, aluminum or stainless steel. Ring 190 is relatively thin, generally having a thickness of from 0.01 centimeters to 0.4 centimeters, preferably 0.05 centimeters. In one embodiment, ring 190 has external diameter of from about 20 centimeters to about 60 centimeters. Those skilled in the art will recognize that the diameter of ring aperture 270 can vary depending on the diameter of ring 190. Stated another way, width 265 of surface 190 varies depending upon the amount of shear force a user desires to generate above test surface 150.

In some embodiments, surface 195 of ring 190 is relatively smooth and relatively flat. The surface 195 is designed to move air generally parallel to the test surface 150 and is not designed to produce thrust or power like a propeller. The surface 195 is not pitched like a propeller and it is not designed to produce thrust or power like a propeller. The surface 195 is configured so that it does not generate airflow normal to the test surface. In some embodiments, for example, those illustrated in FIGS. 7 and 8, the wind shear generating surface 270 is relatively rough like sandpaper with protrusions that range in size from sand-sized grains having approximate diameters of 0.5 cm to larger marble-sized bodies having approximate diameters of 1 cm. Returning now to FIG. 6, the surface 195 of wind shear generating means is positioned at some height above test surface 150, preferably from about 3 centimeters above the test surface 150 to about 5 centimeters above the test surface 150. Those skilled in the art will recognize that the height the wind shear generating surface is above the test surface 150 varies depending upon the amount of the wind shear 310 desired to be generated above test surface 150. A magnitude of wind shear 310 varies with the size of the housing 100 interior 125, the width 265 of ring 190, and the speed that which the surface 195 moves over the test surface. In some embodiments, the height of the wind shear generating surface 195, is variably controlled by the operator.

In one embodiment, skirt 140 is composed of any flexible material such as nylon, rubber or plastic and is attached to housing 100. The skirt 140 may be removably attached. Skirt 140 may be fabricated form any material that is capable of assisting the formation of a seal between the test surface 150 and the skirt 140 such that the amount of air that inadvertently enters the interior chamber 125 of housing 100 is a small fraction of the total air contained in the chamber 125 and preferably from about 0.1% to about 10% of a total volume of air enclosed within the chamber 125 of housing 100. Sealing skirt 140 to test surface 150 is accomplished by using a silicone rubber cement on the surface of the skirt 140 that contacts the test surface 150 or by applying weight to a surface of the skirt 140 that is above the test surface-contacting portion of the skirt 140. Sealing the skirt 140 to test surface 150 is accomplished in the field.

The motor 160 is of conventional construction capable of operating between 200 and 7000 rpm and preferably from about 10 rpm to about 3400 rpm. Preferably, motor 160 is capable of increasing rpm's over time and most preferably, increasing rpm's by about 200 rpm's every 45 seconds.

The shaft 170 is designed by any conventional means to convey power from the motor 160 to either the ring 190 in the case of some embodiments, or to the belt 275 in other embodiments.

The particulate matter monitor 200 is of any conventional design and measures the concentration of small particles, for example, dust particles 325, and relays the measurement to data recording system 230. In one embodiment, particle monitor is model 8520 made by TSI. In some embodiments, device 10 employs a built in particle monitor that utilizes the scattering and absorptive properties of particles to infer their concentration. The data recording system 230 is a computer programmed to record data. The geographical location at which measurements are conducted, are determined by using a Global Positioning Device (GPS) with device 10. Those skilled in the art will recognize that other device suitable for measuring properties of the particles emitted from the test surface as a result of the shear force generated by the shear force generating means, can be used with the device 10 without detracting from the inventive concepts disclosed herein. For example, one embodiment includes a light emitting source and a light-detecting meter. The controller/data recorder can be replaced by an assembly of electronics designed to perform the same basic functions.

In some embodiments, computer 230 is programmed to monitor, record and control the speed of rotation of ring 190. For example, to simulate ever-increasing wind shears above the test surface 150, the an operator controls the variable speed motor 160 to rotate the shaft 170 and the attached ring 190 with gradually increasing rotation rate until some maximum speed as predetermined by the user is reached.

A method for measuring the potential of a test surface to emit windblown dust according to embodiments of the present invention comprises the following steps. Referring now to FIG. 1, a device for measuring the potential of a test surface 150 to emit dust particles is placed over the test surface of interest. Wind shear is generated within the housing 100 by surface 195 and measurements are taken using particle monitor 200.

Other embodiments of the present invention include allowing the user to select the height above the ground at which the wind-generating surface is operated. The selection of the distance can be done either manually or by electronic control. The device may be ventilated using blower 240 and exhaust manifold 250 and the ventilation rate may be monitored. The device may be used in any fluid, either gas or liquid.

It should be understood that the particular embodiments above are only illustrative of the principles of the present invention and various modifications could be made by those skilled in the art, without departing from the scope and spirit of the invention, thus, the scope of the present invention is limited only by the claims that follow.

We claim:

1. An apparatus for measuring soil stability of a test surface comprising:
   a housing defining an interior chamber, said housing having an open bottom wherein the housing is configured to be placed over the test surface;
   a wind shear generating means positioned in relation to said interior chamber, such that the wind shear generating means generates wind shear proximate said test surface and wherein the means for generating wind shear comprises a ring generally parallel to the test surface; and
   at least one particle monitor in communication with the interior chamber.

2. The apparatus of claim 1 wherein a skirt is affixed to the housing.

3. The apparatus of claim 1 further comprising a data recording system.

4. An apparatus for measuring soil stability of a test surface comprising:
   a housing defining an interior chamber, said housing having an open bottom wherein the housing is configured to be placed over the test surface;
   a wind shear generating means positioned in relation to said interior chamber, such that the wind shear generating means generates wind shear proximate said test surface and wherein the means for generating wind shear comprises a belt generally parallel to the test surface; and
   at least one particle monitor in communication with the interior chamber.

5. The apparatus of claim 4 wherein a skirt is affixed to the housing.

6. The apparatus of claim 4 further comprising a data recording system.

7. An apparatus for measuring soil stability of a test surface comprising:
- a housing defining an interior chamber, said housing having an open bottom wherein the housing is configured to be placed over the test surface;
- a wind shear generating means positioned in relation to said interior chamber, such that the wind shear generating means comprises a ring and generates wind shear parallel to said test surface; and
- at least one particle monitor in communication with the interior chamber.

8. An apparatus for measuring soil stability of a test surface comprising:
- a housing defining an interior chamber, said housing having an open bottom wherein the housing is configured to be placed over the test surface;
- a wind shear generating means positioned in relation to said interior chamber, such that the wind shear generating means comprises a belt and generates wind shear parallel to said test surface; and
- at least one particle monitor in communication with the interior chamber.

9. In combination,
- a test surface comprising small particles capable of being emitted in response to a wind shear;
- a wind shear generating means comprising a ring for generating wind shear parallel to the test surface, disposed in an interior chamber of a housing, the housing having an open bottom wherein the housing is configured to be placed proximate the test surface; and
- at least one particle monitor proximate said housing.

10. In combination,
- a test surface comprising small particles capable of being emitted in response to a wind shear;
- a wind shear generating means comprising a belt for generating wind shear parallel to the test surface, disposed in an interior chamber of a housing, the housing having an open bottom wherein the housing is configured to be placed proximate the test surface; and
- at least one particle monitor proximate said housing.

11. A method of measuring a potential of a test surface to emit particles comprising:
- placing a means for generating wind shear over the test surface;
- generating wind shear parallel to the test surface, wherein the means for generating wind shear comprises a ring; and
- using a particle monitor to measure the particles emitted from the test surface.

12. The method of claim 11 further comprising affixing a skirt to the housing.

13. The method of claim 11 further comprising utilizing a data recording system to record particle data.

14. A method of measuring a potential of a test surface to emit particles comprising:
- placing a means for generating wind shear over the test surface;
- generating wind shear parallel to the test surface, wherein the means for generating wind shear comprises a belt; and
- using a particle monitor to measure the particles emitted from the test surface.

15. The method of claim 14 further comprising affixing a skirt to the housing.

16. The method of claim 14 further comprising utilizing a data recording system to record particle data.

* * * * *